US009545523B2

(12) United States Patent
Nanda

(10) Patent No.: US 9,545,523 B2
(45) Date of Patent: Jan. 17, 2017

(54) MULTI-MODALITY TREATMENT SYSTEMS, METHODS AND APPARATUS FOR ALTERING SUBCUTANEOUS LIPID-RICH TISSUE

(71) Applicant: Zeltiq Aesthetics, Inc., Pleasanton, CA (US)

(72) Inventor: Gurvinder Singh Nanda, Fremont, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 719 days.

(21) Appl. No.: 13/830,413

(22) Filed: Mar. 14, 2013

(65) Prior Publication Data

US 2014/0277219 A1 Sep. 18, 2014

(51) Int. Cl.
*A61N 1/32* (2006.01)
*A61N 1/40* (2006.01)
(Continued)

(52) U.S. Cl.
CPC ........... *A61N 1/403* (2013.01); *A61B 18/1402* (2013.01); *A61F 7/02* (2013.01);
(Continued)

(58) Field of Classification Search
CPC .... A61N 1/327; A61N 1/403; A61B 18/1402; A61B 2018/00613; A61B 2018/00023; A61B 2018/143; A61B 2018/1475; A61F 7/00; A61F 7/02; A61F 2007/0052; A61F 2007/0056; A61F 2007/0086; A61F 2007/0239; A61F 2007/0087; A61F 2007/0093; A61F 2007/029
See application file for complete search history.

(56) References Cited

U.S. PATENT DOCUMENTS 681,806 A 9/1901 Mignault et al.
889,810 A 6/1908 Robinson et al.
(Continued)

FOREIGN PATENT DOCUMENTS

AU 2011253768 A1 6/2012
CA 2441489 A1 3/2005
(Continued)

OTHER PUBLICATIONS

"ThermaCool Monopolar Capacitive Radiofrequency, The one choice for nonablative tissue tightening and contouring" Thermage, Inc. Tech Brochure, Nov. 30, 2005, 8 pgs.
(Continued)

*Primary Examiner* — Mark W Bockelman
(74) *Attorney, Agent, or Firm* — Perkins Coie LLP

(57) ABSTRACT

Systems and methods that enable tissue cooling applications and delivery of electrical energy to adipose tissue for alteration and reduction of body fat are described herein. Aspects of the disclosure are directed to, for example, temperature-controlled electroporation of subcutaneous lipid-rich cells. Additional aspects of the disclosure are directed to treatment methods for treating a target region of a human subject's body to achieve an alteration of subcutaneous adipose tissue. The method can include, for example, removing heat from the target region of the human subject during a treatment process to cool subcutaneous lipid-rich cells in the target region to a temperature below normal body temperature. Furthermore, the method can include delivering energy to the target region to produce an electric field in an amount sufficient to create pores in membranes of the subcutaneous lipid-rich cells that have been cooled to the temperature below normal body temperature.

28 Claims, 7 Drawing Sheets

(51) Int. Cl.
*A61F 7/00* (2006.01)
*A61B 18/14* (2006.01)
*A61F 7/02* (2006.01)
*A61B 18/00* (2006.01)

(52) U.S. Cl.
CPC ............ *A61B 2018/00023* (2013.01); *A61B 2018/00613* (2013.01); *A61B 2018/143* (2013.01); *A61B 2018/1475* (2013.01); *A61F 2007/0052* (2013.01); *A61F 2007/0056* (2013.01); *A61F 2007/0086* (2013.01); *A61F 2007/0087* (2013.01); *A61F 2007/0093* (2013.01); *A61F 2007/029* (2013.01); *A61F 2007/0239* (2013.01)

(56) References Cited

U.S. PATENT DOCUMENTS

| | | |
|---|---|---|
| 2,516,491 A | 7/1950 | Swastek |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,282,267 A | 11/1966 | Eidus |
| 3,502,080 A | 3/1970 | Hirschhorn |
| 3,587,577 A | 6/1971 | Zubkov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |

(56) References Cited

U.S. PATENT DOCUMENTS

| | | |
|---|---|---|
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |

(56) References Cited

U.S. PATENT DOCUMENTS

| | | |
|---|---|---|
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |

(56) References Cited

U.S. PATENT DOCUMENTS

| | | |
|---|---|---|
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson et al. |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |

(56) References Cited

U.S. PATENT DOCUMENTS

| | | |
|---|---|---|
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0142469 A1 | 5/2014 | Britva et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2015/0209174 A1 | 7/2015 | Abreu |
| 2015/0216719 A1 | 8/2015 | Debenedictis et al. |
| 2015/0216720 A1 | 8/2015 | Debenedictis et al. |
| 2015/0216816 A1 | 8/2015 | O'Neil et al. |
| 2015/0328077 A1 | 11/2015 | Levinson |
| 2015/0342780 A1 | 12/2015 | Levinson et al. |
| 2016/0051308 A1 | 2/2016 | Pennybacker et al. |
| 2016/0051401 A1 | 2/2016 | Yee et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |

(56) References Cited

FOREIGN PATENT DOCUMENTS

| WO | 0100269 A1 | 1/2001 |
| --- | --- | --- |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 04000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2015117001 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar, G. et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
Al-Sakere, B. et al. "Tumor Ablation with Irreversible Electroporation," PLoS One, Issue 11, Nov. 2007, 8 pages.
Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.
Ardevol, A. et al., "Cooling Rates of Tissue Samples During Freezing with Liquid Nitrogen," Journal of Biochemical and Biophysical Methods, vol. 27, 1993, pp. 77-86.
Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.
Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.
Bohm, T. et al., "Saline-Enhanced Radiofrequency Ablation of Breast Tissue: an in Vitro Feasibility Study," Investigative Radiology, vol. 35 (3), 2000, pp. 149-157.
Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., Chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
International Search Report and Written Opinion for PCT/US2014/026558; Mailed on Oct. 24, 2014, 16 pages.
Isambert, H. "Understanding the Electroporation of Cells and Artificial Bilayer Membranes," Physical Review Letters, vol. 80, No. 15, 1998, pp. 3404-3707.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.

(56) References Cited

OTHER PUBLICATIONS

Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.

Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-; products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

(56) References Cited

OTHER PUBLICATIONS

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Jalian, H. R. et al., "Cryolipolysis: A Historical Perspective and Current Clinical Practice", 32(1) Semin. Cutan. Med. Surg., 2013, pp. 31-34.

Manstein, D. et al., "Selective Cryolysis: A Novel Method of Non-Invasive Fat Removal", 40 Lasers in Surgery & Medicine, 2008, pp. 595-604.

Zelickson, B. et al., "Cryolipolysis for Noninvasive Fat Cell Destruction: Initial Results from a Pig Model", 35 Dermatol. Sug., 2009, pp. 1-9.

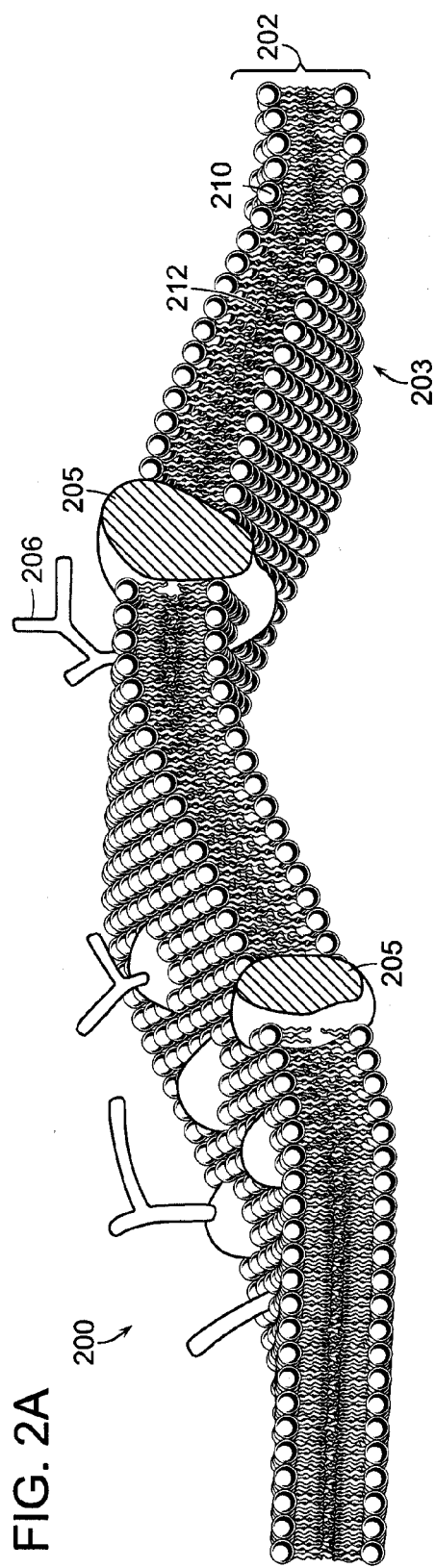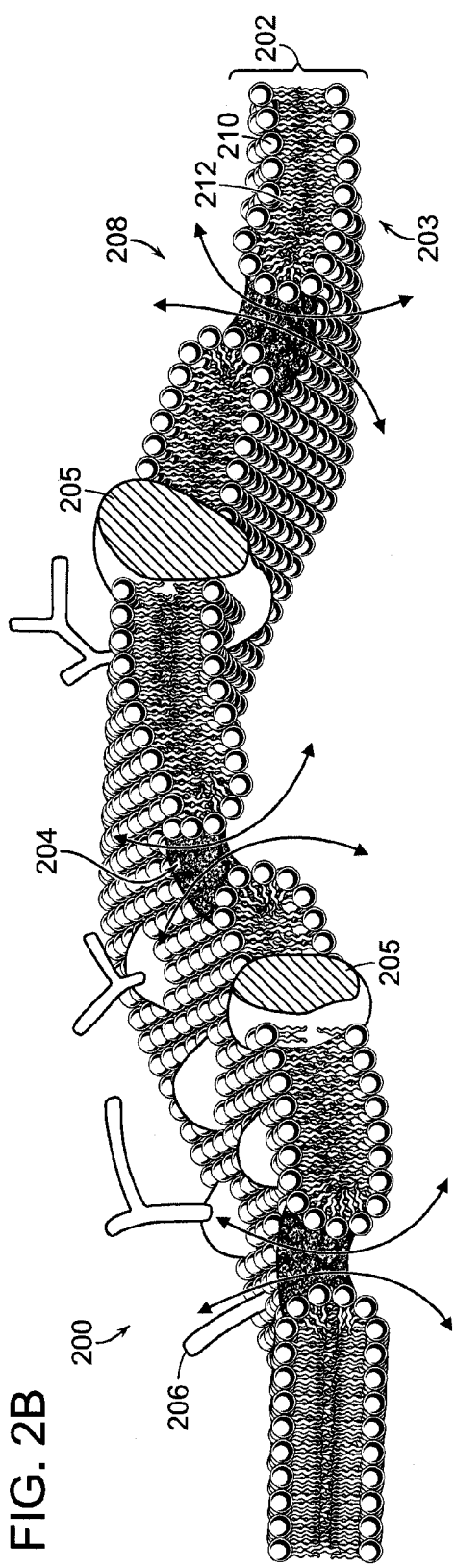
FIG. 2A
FIG. 2B

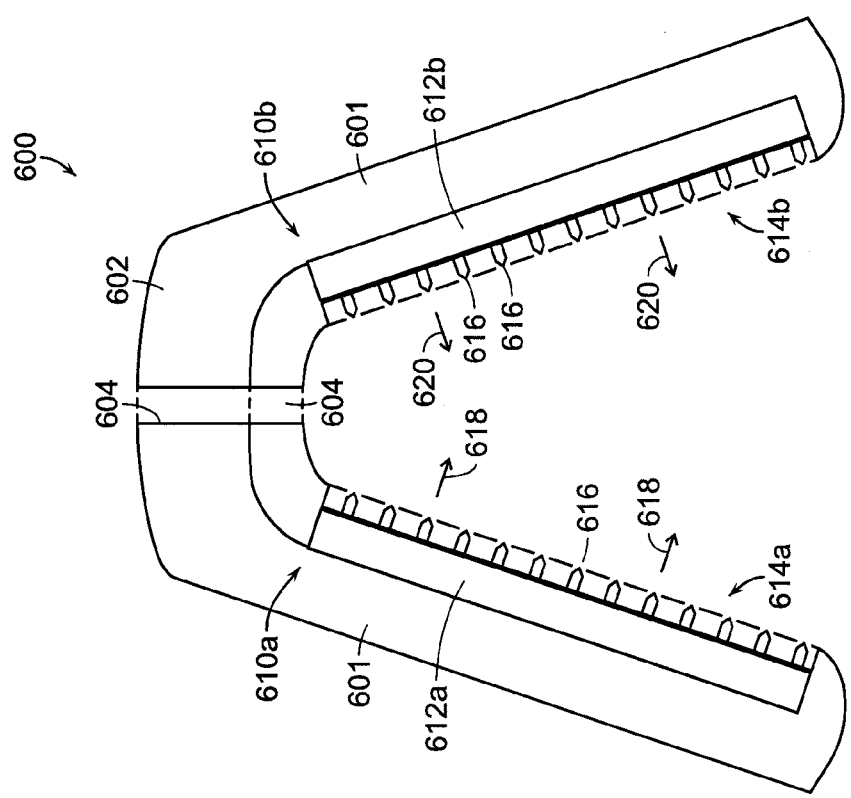
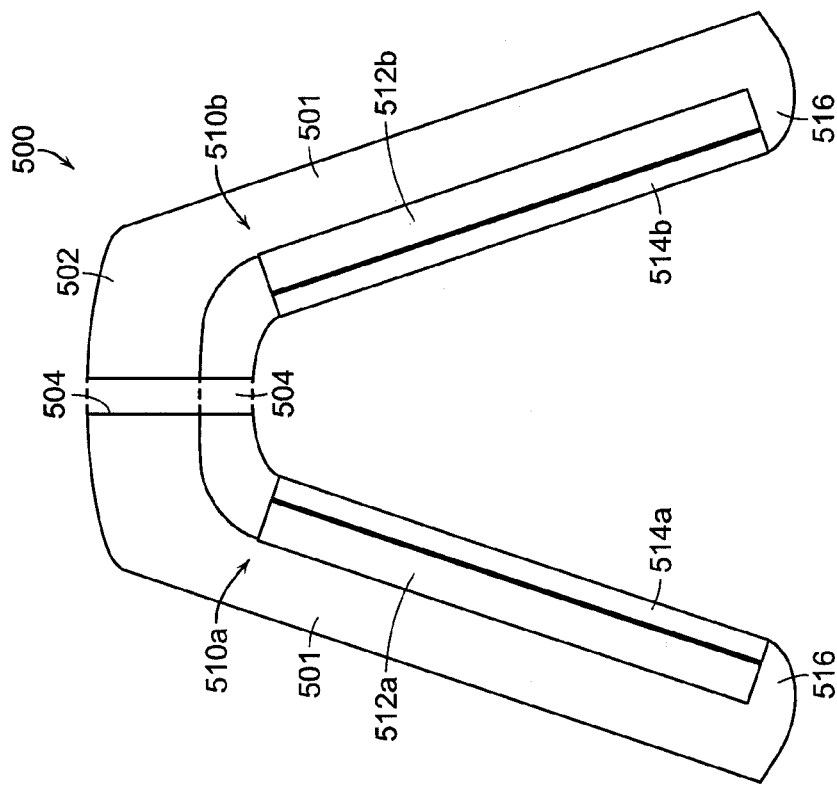

MULTI-MODALITY TREATMENT SYSTEMS, METHODS AND APPARATUS FOR ALTERING SUBCUTANEOUS LIPID-RICH TISSUE

INCORPORATION BY REFERENCE OF COMMONLY-OWNED APPLICATIONS AND PATENTS

The following commonly assigned U.S. patent applications and U.S. patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SUBJECT 11 PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS"; and U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS".

TECHNICAL FIELD

The present application relates generally to multi-modality treatment systems, methods and apparatus for altering tissue (e.g., subcutaneous lipid-rich tissue) including systems and methods for generating electrical fields and removing heat to affect targeted tissue. The present application also relates to temperature-controlled electroporation treatment systems and methods for altering targeted tissue.

BACKGROUND

Excess body fat, or adipose tissue, may be present in various locations of the body, including, for example, the thigh, buttocks, abdomen, knees, back, face, arms, and other areas. Excess adipose tissue can detract from personal appearance and athletic performance. Moreover, excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be cosmetically unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 2A and 2B are schematic cross-sectional views of the lipid bilayer of a cell membrane shown (A) before and (B) after applying energy sufficient to create pores in the lipid bilayer.

FIG. 5 is a partial cross-sectional view illustrating a multi-modality applicator suitable to be used in the system of FIG. 1 in accordance with another embodiment of the technology.

FIG. 6 is a partial cross-sectional view illustrating a multi-modality applicator suitable to be used in the system of FIG. 1 in accordance with a further embodiment of the technology.

DETAILED DESCRIPTION

A. Overview

Figure 1:
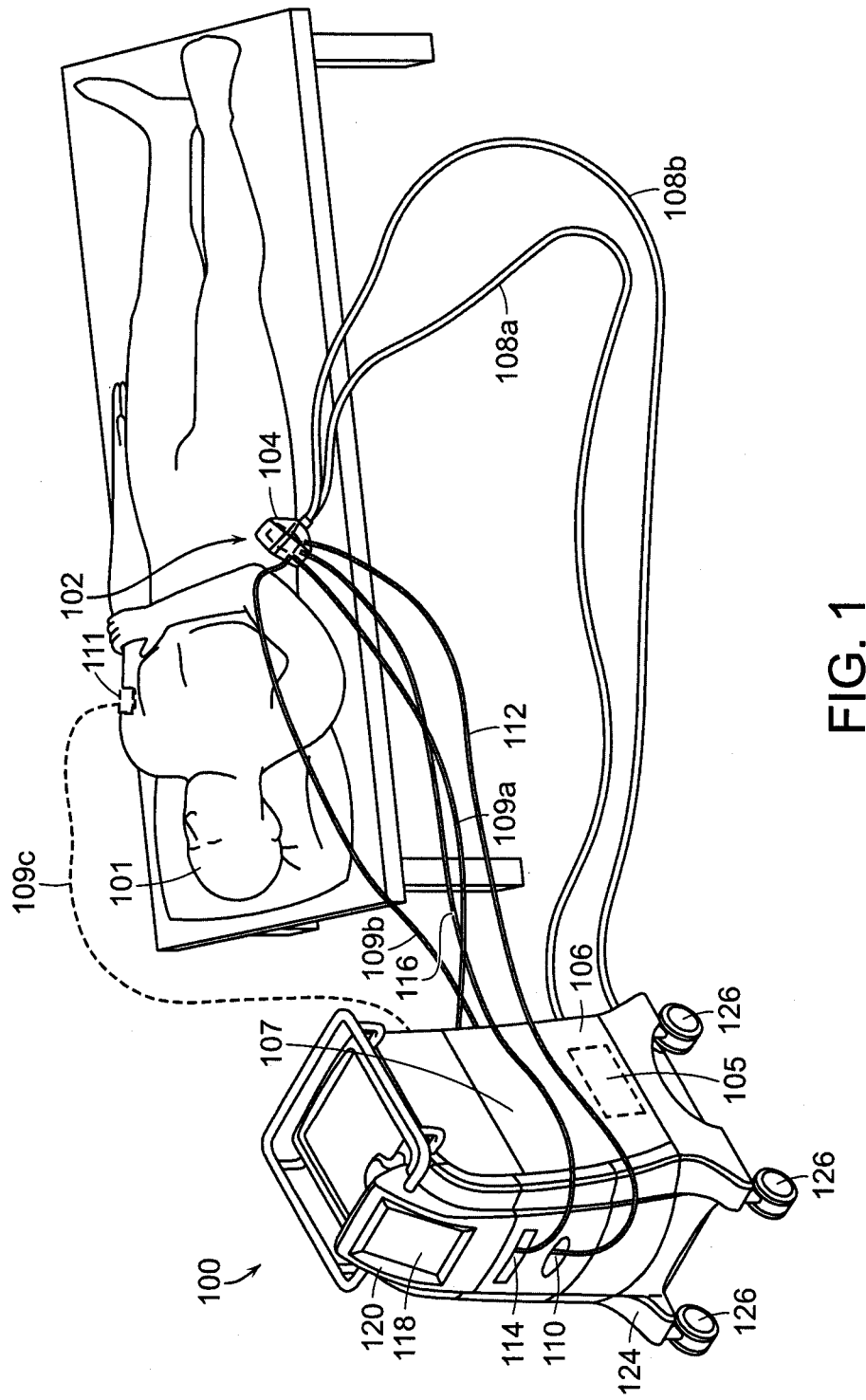
FIG. 1 is an isometric view schematically illustrating a treatment system for treating subcutaneous lipid-rich regions of a patient in accordance with an embodiment of the disclosure.

Systems, devices and methods are provided herein that enable simultaneous or sequential cooling and delivery of energy to a target region selectively to affect targeted cells. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the claimed technology.

As used herein, the terms "bipolar" and "monopolar" can refer to an electrode configuration or in other embodiments to an electrical pulse, or pulse waveform. For example, a "bipolar electrode configuration" or "bipolar configuration" can refer to having two or more electrodes between which an electric field can be generated. In other embodiments, "bipolar" can refer to the waveform of an electrical signal generated and/or delivered to two or more electrodes, and such as described in U.S. Pat. No. 7,054,685, which is incorporated herein by reference in its entirety. Likewise, "monopolar electrode configuration" or monopolar configuration" can refer to having one or more electrodes that generate an electric field that can dissipate at a particular depth or distance away from the electrode(s). "Monopolar" can also refer to the electrical pulse or waveform generated and delivered to the electrode(s), such as described further in U.S. Pat. No. 7,054,685.

Some embodiments of the disclosure are directed to a system for affecting lipid-rich cells in a region of a human subject's body. The system can include a treatment unit configured to house a coolant. In one embodiment, the treatment unit can be in thermal communication with a fluid chamber for holding the coolant. The system can also include an energy generating unit, for example for generating electrical pulses, and an applicator in fluid communication with the treatment unit and in electrical communication with the energy generating unit. The system can further include a controller in communication with the treatment unit and the energy generating unit. In one embodiment, the controller has instructions for causing the applicator to reduce a temperature of (e.g., extract heat from) a target region beneath the epidermis of the subject to reduce a temperature of subcutaneous lipid-rich cells in the target region to a second temperature less than 37° C. After reducing the temperature of the target region, the instructions can cause the applicator to apply energy across the target region to form pores in membranes of the subcutaneous lipid-rich cells. In one embodiment, the instructions can cause the applicator to apply voltage across the target region to produce a pulsed electric field in an amount sufficient to form the pores.

Other aspects of the disclosure are directed toward a temperature-controlled electroporation treatment system for cosmetically altering a target region of a human subject's body to achieve a cosmetically beneficial alteration of tissue, such as subcutaneous adipose tissue. The temperature-controlled electroporation treatment system can include a treatment unit in thermal communication with a fluid chamber. The temperature-controlled electroporation treatment system can also include an electroporation energy source, a controller and an applicator. The applicator can include a first electrode and a second electrode in electrical communication with the electroporation energy source and a cooling element in communication with the treatment unit. In one embodiment, the controller includes instructions that cause the applicator to remove heat from the target region of the subject to reduce a natural body temperature to a lower temperature. The controller can also include instructions that cause the applicator to deliver an electric field through the target region such that subcutaneous lipid-rich cells at the target region are substantially affected while non-lipid-rich cells at the target region are not substantially affected. The controller can further include instructions that cause the applicator to maintain the lower temperature for a period after the electric field is removed.

Additional embodiments of the disclosure are directed to cosmetic methods for affecting a target region of a human body to achieve a cosmetically beneficial alteration. For example, the method can include removing heat from the target region of the human subject to cool subcutaneous lipid-rich cells in the target region to a temperature below normal body temperature. The method can also include delivering energy to the target region to produce an electric field in an amount sufficient to create pores in membranes of the subcutaneous lipid-rich cells that have been cooled to the temperature below normal body temperature. The pores can compromise cell volume and/or cell viability, and the method can thereby achieve a cosmetically beneficial alteration of subcutaneous adipose tissue.

Some of the embodiments disclosed herein can be for cosmetically beneficial alterations of a variety of body regions. As such, some treatment procedures may be for the sole purpose of altering the body region to conform to a cosmetically desirable look, feel, size, shape or other desirable cosmetic characteristic or feature. Accordingly, at least some embodiments of the cosmetic procedures can be performed without providing any, or in another embodiment, providing minimal therapeutic effect. For example, some treatment procedures may be directed to treatment goals that do not include restoration of health, physical integrity, or the physical well being of a subject. In other embodiments, however, the cosmetically desirable treatments may have therapeutic outcomes (whether intended or not), such as, psychological benefits, alteration of body hormones levels (by the reduction of adipose tissue), etc. The cosmetic methods can target subcutaneous regions to change a subject's appearance such as, for example, procedures performed on a subject's "love-handles" (i.e., excess adipose tissue at the side of a subject's waistline).

B. Multi-Modality Treatment System

FIG. 1 and the following discussion provide a brief, general description of an example of a suitable multi-modality treatment system 100 in which aspects of the disclosure can be implemented. In some embodiments, the multi-modality treatment system 100 can be a temperature-controlled electroporation treatment system. Those skilled in the relevant art will appreciate that other examples of the disclosure can be practiced with other treatment systems and treatment protocols, including invasive, minimally invasive, other non-invasive medical treatment systems, and/or combinations of one or more of the above for treating a subject 101. In general, the term "treatment system", as used generally herein, refers to any of the above-referenced categories of medical treatment systems as well as any treatment regimes or medical device usage.

In one embodiment, the multi-modality treatment system 100 is suitable for altering a human subject's subcutaneous adipose tissue, including such as by cooling and/or by delivering energy. The term "subcutaneous tissue" means tissue lying beneath the dermis and includes subcutaneous fat, or adipose tissue, which primarily is composed of lipid-rich cells, or adipocytes. Such alteration (e.g., by cooling, energy delivery and/or combination of cooling and energy delivery) is believed to be an intermediate and/or final result of one or more mechanisms acting alone or in combination. It is thought that such mechanism or mechanisms can trigger an apoptotic cascade, which is believed to be the dominant form of lipid-rich cell death by non-invasive cooling alone or in combination with other forms of cell interrogation.

In several embodiments, apoptosis of the subcutaneous lipid-rich cells in the region of the subject 101 being treated is a desirable outcome for beneficially altering (e.g., sculpting and/or reducing) adipose tissue. Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990). One aspect of apoptosis, in contrast to cellular necrosis (a traumatic form of cell death causing local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other possible mechanisms of adipocyte damage, described in U.S. Pat. No. 8,192,474, relates to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation while pulled into, e.g., a vacuum cup, or simply as a result of the cooling which may affect vasoconstriction in the cooled tissue. In addition to the ischemic damage caused by oxygen starvation and the build up of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

When cooling the subcutaneous tissues to a temperature lower than 37° C., subcutaneous lipid-rich cells can selectively be affected. In general, the epidermis and dermis of the subject 101 have lower amounts of lipids compared to the underlying lipid-rich cells forming the subcutaneous tissues. Because non-lipid-rich cells usually can withstand colder temperatures better than lipid-rich cells, the subcutaneous lipid-rich cells selectively can be affected while maintaining the integrity of the non-lipid-rich cells in the dermis and/or epidermis. In some embodiments, the multi-modality treatment system 100 can cool the skin of the patient to a temperature in a range of from about −20° C. to about 20° C. In other embodiments, the cooling temperatures can be from about −20° C. to about 10° C., from about −15° C. to about 5° C., or from about −10° C. to about 0° C.

Without being bound by theory, the selective effect of cooling on lipid-rich cells is believed to result in, for example, membrane disruption, shrinkage, disabling, destroying, removing, killing, or another method of lipid-rich cell alteration. Depending on the duration and final cooling temperature, subcutaneous lipid-rich cells can selectively become altered in a manner that makes the cells more susceptible to further interrogation and/or cell injury than non-lipid-rich cells in the same region. Such alteration (e.g., by cooling, energy delivery and/or combination of cooling and energy delivery) is believed to be an intermediate and/or final result of one or more mechanisms acting alone or in combination. It is thought that such mechanism or mechanisms can trigger an apoptotic cascade, which is believed to be the dominant form of lipid-rich cell death by non-invasive cooling alone or in combination with other forms of cell interrogation. Temperature exposures and/or other energy delivery modalities that elicit these apoptotic events in lipid-rich cells may contribute to long-lasting and/or permanent reduction and reshaping of subcutaneous adipose tissue.

One form of cell interrogation is electroporation, or electropermeabilization, which refers to the permeabilization of a cell membrane as a consequence of the application of electric fields. The electric fields can be pulsed or continuous. Short and intense electric fields across the cell membrane, the cells or the tissues can cause permeabilization. The permeabilization can be temporary (e.g., reversible permeabilization) or permanent (e.g., irreversible permeabilization) based on the electric field magnitude, electric field duration, number of pulses, frequency of pulse, duration of pulses, or the like.

FIGS. 2A and 2B are schematic cross-sectional views of a lipid bilayer 202 of a cell membrane 200 shown before (FIG. 2A) and after (FIG. 2B) applying an external energy sufficient to create (e.g., open) pores 204 in the lipid bilayer 202, a basic component of plasma membranes of almost all living organisms, including humans. Referring to FIGS. 2A and 2B together, the cell membrane 200 can include the lipid molecules 203 of the cell's lipid bilayer 202, proteins 205 and cell surface carbohydrates 206. During electroporation, the lipid molecules 203 of the lipid bilayer 202 shift positions. This shift creates pores 204 which act as conductive pathways 208 through the bilayer 202 as it is filled with water and/or interstitial fluid. A lipid bilayer 202 has a strongly polar and hydrophilic (polar) head region 210 represented by phosphate groups and a strongly nonpolar and hydrophobic (nonpolar) tail region 212 represented by fatty acid chains. The lipid bilayer 202 is configured so that the tail regions 212 are isolated from the surrounding polar fluid while the more hydrophilic head regions 210 are associated with the intracellular and extracellular faces of the bilayer. This alignment of head 210-to-tail 212 regions result in, among other things, an electric potential (the "trans-membrane potential") at the point where the regions 210, 212 meet. When an electric field is applied at a voltage higher than that potential, a focused pulse (FP) of current disturbs it. As shown in FIG. 2B, some head regions 210 and tail regions 212 will then separate; some will "flip" end-for-end. As the bonds between head and tail regions fail, the pores 204 can form in the cell membrane 200. Without being bound by theory, it is believed that the pores 204 formed in the lipid bilayer 202 allow for cell lysis, intracellular content outflow from the cells, and/or fluid exchange with interstitial fluid that can trigger an apoptotic cascade or other form of cell death (e.g., necrosis).

Delivery of energy, such as high voltage or low voltage energy, to subcutaneous tissue to generate an electric field across the tissue selectively can increase the electrical conductivity and permeability of the cell plasma membranes of the lipid-rich cells. For a given pulse duration and shape, a specific transmembrane voltage or energy threshold exists for the manifestation of the electroporation phenomenon (e.g., from about 0.5 V to about 1 V, from about 1 V to about 2 V, or from about 2 V to about 5 V per cell). Accordingly, there is an electric field magnitude threshold for electroporation wherein only the cells exposed to an electric field equal to or greater than a first, lower electroporation threshold of the specific cell, can be electroporated (e.g., pores form and/or open in the cell membrane). Above the first, lower electroporation threshold, the number of pores and/or the pore diameter increases with both the amplitude and duration of the electric field pulses. Removing the electric field pulses enables the induced pores to reseal. Depending on the number, diameter and life time of pores in the membrane, electroporation of the cell may result in significant injury to the cell that can trigger an apoptotic cascade event and eventual cell death. Cells also have a second, upper electroporation threshold which, if exceeded, will compromise the viability of the cells (e.g., the membrane pores will irreversibly be open). If cells become permanently permeable from the formation of pores in the cell membrane, the cells are unable to repair the damage and die due to a loss of homeostasis.

The first, lower electroporation threshold is different for different cells and depends in part on cell size in that the larger the cell size (e.g., as determined by cell volume), the lower the electroporation threshold. For example, the larger the cell, the smaller the electric field required to induce pore formation. Accordingly, larger cells such as lipid-rich cells can selectively be electroporated (reversibly or irreversibly) with external application of electric fields that are lower in magnitude when compared to the magnitude of electric fields required to also electroporate smaller cells (e.g., non-lipid-rich cells).

As described in more detail herein, selective cooling of subcutaneous lipid-rich cells can alter the lipid-rich cells such that these cells are more susceptible to cell injury and interrogation. For example, cooling of subcutaneous lipid-rich cells (e.g., to a temperature below normal body temperature) can lower a transmembrane voltage or energy threshold for the subcutaneous lipid-rich cells such that less energy is required to induce pore formation than would be necessary if the lipid-rich cells were not cooled. In specific examples, the energy required to induce pore formation in cooled subcutaneous lipid-rich cells can be approximately 5% to approximately 50% lower, or in another embodiment approximately 10% to approximately 30% lower, than the energy required to induce pore formation in the non-cooled lipid-rich cells. In other embodiments, the energy required to induce pore formation in cooled subcutaneous lipid-rich cells can be approximately 10%, 15%, 20%, 25% or 30% lower the energy required to induce pore formation in the non-cooled lipid-rich cells. In a further embodiment, cooling subcutaneous lipid-rich cells can lower a transmembrane voltage threshold of the subcutaneous lipid-rich cells by an amount approximately greater than 10%, approximately greater than 20%, or approximately greater than 30%. Accordingly, electrical energy can be subsequently and/or concurrently applied to the target tissue to generate a pulsed electric field that can further selectively disrupt subcutaneous lipid-rich cells and can be delivered at a magnitude that is lower than would otherwise be necessary to induce lipid-rich cell damage and/or death by electroporation. For example, the magnitude of electric field and duration of application sufficient to alter cooled subcutaneous lipid-rich cells can be at a clinically acceptable voltage range (e.g., between approximately 50 V to about 900 V) for noninvasive and cosmetically beneficial treatment and/or reduction in subcutaneous adipose tissue.

In some aspects of the present technology, the subcutaneous tissue can be cooled to a temperature lower than 37° C., which disproportionately affects the lipid-rich cells in the tissue—either injuring them or making them more susceptible to further injury and interrogation. Cooling can be maintained during subsequent application of a pulsed electric field in an amount sufficient to create (e.g., form, open, etc.) pores in membranes of the subcutaneous lipid-rich cells. In further embodiments, cooling can be continued after the pulsed electric field is discontinued or removed to maintain membrane pore stability post-electroporation to promote further cell lysis and/or injury. In other embodiments, cooling and energy delivery can be applied in different protocols. For example, cooling can precede delivery of the pulsed electric field, but be discontinued before or during the electroporation portion of the treatment.

Figure 3B:
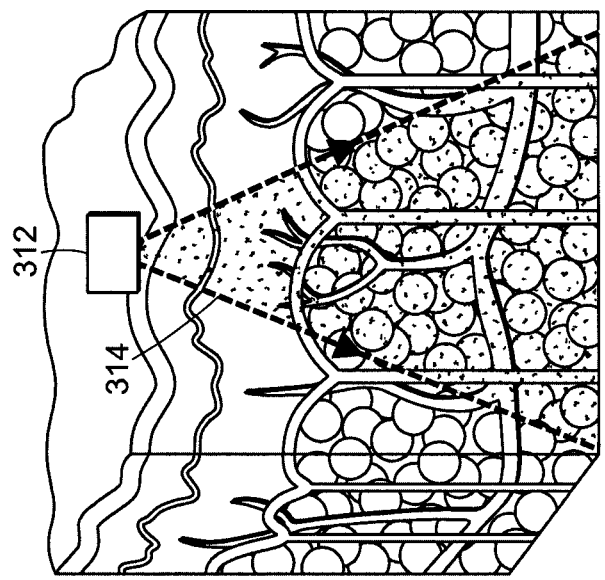
FIGS. 3A and 3B are schematic cross-sectional views of the skin and subcutaneous tissue of a subject illustrating the application of (A) bipolar and (B) monopolar electrical pulses thereto.
Figure 3A:
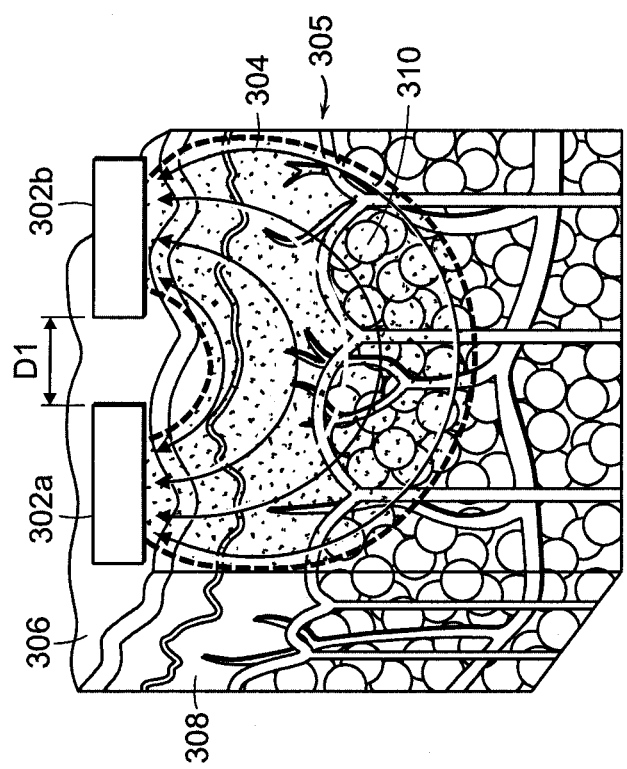

As described above, cooling the subcutaneous tissues to a temperature lower than 37° C. selectively can affect lipid-rich cells. Cooling the lipid-rich cells of the subcutaneous layer tends uniformly to affect the adipose cells distributed throughout the subcutaneous tissue at a given depth below the dermis, for instance, when such lipid-rich cells are cooled non-invasively. Accordingly, in one embodiment, the multi-modality treatment system 100 (FIG. 1) is configured to not only cool subcutaneous tissue as described herein but also to deliver energy for generating an electric field, for example to selectively electroporate certain adipose tissue according to the methods described herein. One method of selectively electroporating such tissue is by the delivery of high voltage or low voltage electrical pulses, including for example bipolar electrical pulses or unipolar electrical pulses, to the subcutaneous tissue selectively to form pores in the lipid bilayer of subcutaneous lipid-rich cell membranes. FIGS. 3A and 3B are schematic perspective views in cross-section of the skin and subcutaneous tissue of a subject illustrating the application of (A) bipolar and (B) monopolar (e.g., unipolar) electrical pulses thereto.

As shown in FIG. 3A and in a bipolar electrode configuration, current passes between two electrodes 302*a*, 302*b* located a predetermined distance $D_1$ apart from each other. The electrical field 304 applied to the region to be treated and the propagation of the current is limited to the region adjacent to and between the electrodes 302*a*, 302*b*. FIG. 3A shows a schematic depiction of the application of energy for generating an electric field 304 to a target tissue region 305 having epidermal 306, dermal 308 and subcutaneous adipose tissue 310. Bipolar rectangular pulses at high frequency, low frequency and/or long or short duration can be employed. For example, a treatment protocol can be predetermined that takes into account a lipid-rich cell's survivability limit which can depend on, for example, the combination of electric field amplitude (e.g., strength), pulse frequency, and duration of pulses. Both directions of the electric field, meaning both positive (+) and negative (−) polarities, are capable of creating pores, or enlarging pores, in the cell membranes of target cells exposed to the electric field. Rectangular bipolar pulses that are balanced, e.g., from two pulses each of opposite polarity, can also be generated, for example, using a pulse generator that has a direct current blocking capacitor.

In another embodiment shown in FIG. 3B, monopolar or unipolar pulsing (e.g., from a single electrode 312) that carries a direct current component 314 into the treated tissue can also be employed along with a sleeve or dielectric layer (not shown) to prevent electrolytic effects between the interface of the electrode 312 and tissues (e.g., prevent metal depositions from the electrodes, prevent chemical decompositions of tissue during treatment, etc.).

Other methods of applying energy selectively to alter subcutaneous tissue as described herein may be used in addition to or in place of cooling combined with electroporation, including, e.g., radiofrequency (RF) energy, optical (e.g., laser light), acoustic (e.g., ultrasound, high-frequency ultrasound), infrared, microwave, etc.

In the treatment therapy associated with the embodiments described herein, the treatment parameters may be adjusted to affect, in connection with cooling the subcutaneous tissue, the temperature profile of and the number of the adipose cells in the subcutaneous tissue within the target region that are electroporated via the application of such an electric field or interrogated by another external energy modality. For example, applied energy in the range of about 50 V to about 1000 V or lower after or during cooling can have the desired effect of selectively altering or reducing subcutaneous adipose tissue in the target region.

In some embodiments, the multi-modality treatment system 100 can be configured to apply cooling treatment before and/or during application of energy to the skin of the subject 101 to generate an electric field in a simultaneous manner, or in a sequential manner, such that the subcutaneous lipid-rich cells are cooled to a temperature less than 37° C. In other embodiments, the cooling temperatures can be from about −20° C. to about 20° C., from about −20° C. to about 10° C., from about −15° C. to about 5° C., or from about −10° C. to about 0° C.

In additional embodiments, the multi-modality treatment system 100 can be configured to apply cooling treatment and/or to maintain cooling treatment after the subcutaneous lipid-rich cells have been electroporated. For example, heat can be removed from the target region to reduce a natural body temperature to a lower temperature in the target region, and then the lower temperature can be maintained for a period (e.g., time) after the electric field is removed. In one embodiment the period can be between about 1 minute and about 2 hours, between about 1 minute and about 1 hour, between about 1 minute and about 50 minutes, between about 1 minute and about 40 minutes, between about 1 minute and about 30 minutes, or between about 1 minute and about 20 minutes. Other periods of time can be used. Still another embodiment results in maintaining the lower temperature for between about 5 minutes and about 15 minutes post-electroporation. In other embodiments, the electric field can be applied to the target region of the subject 101 simultaneously with cooling (i.e., removing heat), before, periodically during, or after cooling for selectively affecting the lipid-rich cells in the subcutaneous layer of the subject 101.

In various embodiments, the multi-modality treatment system 100 includes a controller, a computing device, a data acquisition device, a chiller, and one or more multi-modality applicators. These components can be implemented in various embodiments to apply selected treatment profiles to a subject 101 (e.g., a human or an animal) for reducing or altering adipose tissue.

Referring again to FIG. 1, the multi-modality treatment system 100 can non-invasively remove heat from subcutaneous lipid-rich target areas of the subject 101 and can non-invasively or minimal-invasively apply energy to generate an electric field selectively to electroporate subcutaneous lipid-rich cells in the target area in accordance with an embodiment of the technology. The system 100 can include a multi-modality applicator 104 that engages a target region of the subject 101, such as the abdominal region 102. It will be understood that multi-modality applicators 104 can be provided having various shapes and sizes suitable for different body regions and body parts such that heat can be removed from and/or an external energy can be applied to any subcutaneous lipid-rich target area of the subject 101.

An applicator 104 is a component of the system 100 that both cools subcutaneous tissue and selectively applies energy to (e.g., electroporates) lipid-rich cells in a subcutaneous region of a subject 101 (i.e., "patient"). Various types of applicators may be applied during treatment, such as a vacuum applicator, a belt applicator (either of which may be used in combination with a massage or vibrating capability), and so forth. Each applicator 104 may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators and their configurations usable or adaptable for use with the multi-modality treatment system 100 variously are described in, e.g., commonly assigned U.S. Pat. No. 7,854,754 and U.S. Patent Publication Nos. 2008/0077201, 2008/0077211 and 2008/0287839. In further embodiments, the system 100 may also include a patient protection device (not shown) incorporated into or configured for use with the applicator 104 that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

In the present example, the system 100 can also include a treatment unit 106 and supply and return fluid lines 108a-b between the multi-modality applicator 104 and the treatment unit 106. A treatment unit 106 is a device that can increase or decrease the temperature at a connected multi-modality applicator 104 that is configured to engage the subject and/or the target region of the subject. The treatment unit 106 can remove heat from a circulating coolant to a heat sink and provide a chilled coolant to the multi-modality applicator 104 via the fluid lines 108a-b. Alternatively, the treatment unit 106 can circulate warm coolant to the multi-modality applicator 104 during periods of warming. In further embodiments, the treatment unit 106 can circulate coolant through the multi-modality applicator 104 and increase or decrease the temperature of the multi-modality applicator by controlling power delivery to one or more Peltier-type thermoelectric elements incorporated within the multi-modality applicator. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. In one embodiment, the treatment unit 106 can include a fluid chamber 105 configured to house and provide the coolant. Alternatively, a municipal water supply (e.g., tap water) can be used in place of or in conjunction with the treatment unit 106. In a further embodiment, the multi-modality applicator 104 can be a fluid-cooled applicator capable of achieving a desired temperature profile such as those described in U.S. patent application Ser. No. 13/830,027 (U.S. Pub. No. 2014/0277302), filed Mar. 14, 2013, and incorporated herein by reference in its entirety. One skilled in the art will recognize that there are a number of other cooling technologies that could be used such that the treatment unit, chiller, and/or applicator need not be limited to those described herein.

The system 100 can further include an energy generating unit 107, such as an electroporation pulse generator, and power lines 109a-b between the applicator 104 and the energy generating unit 107. In other embodiments (e.g., having a monopolar configuration), the system 100 can include a current return electrode 111 located separately from the applicator 104; power line 109c (shown in dotted line) can electrically connect the return electrode 111, if present, and the energy generating unit 107. The energy generating unit 107 can include an electroporation pulse generator, such as a high voltage or low voltage pulse generator, capable of generating and delivering a high or low voltage current, respectively, through the power lines 109a, 109b to one or more electrodes (e.g., cathode, anode) in the multi-modality applicator 104 for generating and delivering a pulsed electric field to the target region of the subject 101, wherein the pulsed electric field strength exceeds a transmembrane potential of a subcutaneous lipid-rich cell. In other embodiments, the energy generating unit 107 can include a variable powered RF generator capable of generating and delivering RF energy, such as RF pulses, through the power lines 109a, 109b or to other power lines (not shown). In a further embodiment, the energy generating unit 107 can include a microwave pulse generator, an ultrasound pulse laser generator, or high frequency ultrasound (HIFU) phased signal generator, or other energy generator suitable for applying energy, for example, to further interrogate cooled lipid-rich cells in subcutaneous layers. In additional embodiments, the system 100 can include more than one energy generator unit 107 such as any one of a combination of the energy modality generating units described herein.

A dielectric element (e.g., layer or film) may be used on the one or more electrodes to increase the impedance of the electrode and produce a more uniform current flow through the electrode(s) to the skin of the subject 101. Such an element creates a capacitance effect whose magnitude and other qualities may be controlled by the composition, surface area and thickness of the layer, the choice of methods by which the layer or film is deposited and/or adhered to the electrode, and/or the frequency of the signal. Alternatively, the system 100 can be configured to use an electrode without a dielectric element. The choice of whether to use a dielectric element may be predicated upon the particular design of the electrode, the location on the patient which the system 100 is used, frequency and power settings, temperatures, treatment duration, and other such parameters and other considerations.

In the illustrated example, the multi-modality applicator 104 is associated with at least one treatment unit 106. The applicator 104 can provide mechanical energy to create a vibratory, massage, and/or pulsatile effect. The applicator 104 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy or other mechanical energy to the treatment site. Further examples include a plurality of actuators for use in connection with a single multi-modality applicator 104 in any desired combination. For example, an eccentric weight actuator can be associated with one section of a multi-modality applicator 104, while a pneumatic motor can be associated with another section of the same applicator 104. This, for example, would give the operator of the multi-modality treatment system 100 options for differential treatment of lipid-rich cells within a single region or among multiple regions of the subject 101. The use of one or more actuators and actuator types in various combinations and configurations with a multi-modality applicator 104 may be possible.

The multi-modality applicator 104 can include one or more heat exchanging units. Each heat exchanging unit can include or be associated with one or more Peltier-type thermoelectric elements, and the multi-modality applicator 104 can have multiple individually controlled heat exchanging zones (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Applicators having multiple individually controlled heat exchanging units are described in commonly assigned U.S. Patent Publication Nos. 2008/0077211 and 2011/0238051.

Additionally, the multi-modality applicator 104 can include one or more electrodes, such as flat plate electrodes for delivering electrical pulse or pulses to the target region. For example, the electrodes can be a single electrode or a plurality of electrodes positioned in a desired or segmented arrangement and, in some embodiments, can form a segmented flexible circuit. Electrical pulses can be delivered to the electrodes at a predetermined voltage, frequency and duration via the power lines 109a, 109b and, thereafter, coupled to the target region of the subject 101 to generate an electric field sufficient to create and, in some embodiments, maintain open pores in membranes of the subcutaneous lipid-rich cells. Generally, electrodes can be arranged in monopolar or bipolar configurations. When using bipolar electrodes, the current passes through the tissue of the target region and between two electrodes located a predetermined distance apart. While the propagation of the current is limited to the region generally between the electrodes themselves, bipolar electrode configurations can provide a suitable distribution of energy and generate pore formation and growth on multiple sides of cell membranes. While not being bound by theory, useful ranges of applied voltage, frequency and pulse duration in such a bipolar electrode configuration can, in some embodiments and with use of some applicators, devices and systems, be between about 5 V/cm to 200 V/cm, 10 kHz to 100 kHz, and 1 millisecond (msec) to 100 msec, respectively. In other embodiments, useful ranges of applied voltage, frequency and pulse duration for a bipolar electrode configuration can be between about 200 V/cm to 1,500 V/cm, 50 kHz to 1 MHz, and 10 microseconds (μsec) to 1 msec, respectively. In further embodiments, useful ranges of applied voltage, frequency and pulse duration can be about 10 V/cm to 1 kV/cm, 50 kHz to 5 MHz, and 1 msec to 10 seconds, respectively. Other ranges of applied voltage, frequency, pulse duration as well as other electric pulse characteristics including waveform shape (square, triangular, circular, exponential, etc.) and time delay in a pulse sequence, are possible, such as those described in U.S. Pat. No. 7,054,685.

Monopolar electrode configurations are configured to have current flow from an electrode within the multi-modality applicator 104 into the epidermis and dermis, through the subcutaneous tissue until it reaches a location wherein it has dissipated to a level that it does not have any appreciable effect. The current generated by a monopolar electrode can generate an electric field sufficient to form pores in membranes of the subcutaneous lipid-rich cells (e.g., on at least one side of the cell membrane) where it then continues to flow through the body to the return electrode 111. The return electrode 111 can be adhered to a second site on the subject 101 and the current can return to the energy generating unit 107 via the power line 109c. Alternatively, the multi-modality applicator 104 may operate without a return electrode and power return line. At sufficiently high RF frequencies (e.g., greater than about 1 MHz), the return current can flow out of the body and through the air to the energy generating unit 107 to complete the circuit. While not being bound by theory, useful ranges of applied voltage, frequency and pulse duration in such a configuration, sometimes referred to a "unipolar" configuration, can be between about 1 kV to 30 kV, 1 MHz to 60 MHz, and 100 μsec to 100 msec, respectively. In other embodiments and with use of some applicators, devices and systems, useful ranges of applied voltage, frequency and pulse duration for a monopolar electrode configuration can be between about 100 V to 1 kV, 20 kHz to 200 kHz, and 10 μsec to 1 msec, respectively. In further embodiments, useful ranges of applied voltage, frequency and pulse duration can be about 50 V to 500 V, 50 kHz to 10 MHz, and 1 msec to 10 seconds, respectively.

The system 100 can further include a power supply 110 and a controller 114 operatively coupled to the multi-modality applicator 104. In one embodiment, the power supply 110 can provide a direct current voltage to the applicator 104 to remove heat from the subject 101. The controller 114 can monitor process parameters via sensors (not shown) placed proximate to the multi-modality applicator 104 via a control line 116 to, among other things, adjust the heat removal rate and/or energy delivery rate based on the process parameters. The controller 114 can further monitor process parameters to adjust the applicator 104 based on treatment parameters, such as treatment parameters defined in a custom treatment profile or patient-specific treatment plan, such as those described, for example, in commonly assigned U.S. Pat. No. 8,275,442.

The controller 114 can exchange data with the applicator 104 via an electrical line 112 or, alternatively, via a wireless or an optical communication link. Note that control line 116 and electrical line 112 are shown in FIG. 1 without any support structure. Alternatively, control line 116 and electrical line 112 (and other lines including, but not limited to fluid lines 108a-b and power lines 109a-b) may be bundled into or otherwise accompanied by a conduit or the like to protect such lines, enhance ergonomic comfort, minimize unwanted motion (and thus potential inefficient removal of heat from and/or delivery of energy to subject 101), and to provide an aesthetic appearance to the system 100. Examples of such a conduit include a flexible polymeric, fabric, or composite sheath, an adjustable arm, etc. Such a conduit (not shown) may be designed (via adjustable joints, etc.) to "set" the conduit in place for the treatment of the subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, an audio component such as a microphone, or any other device suitable for accepting user input. The output device 120 can include a display or touch screen, a printer, video monitor, a medium reader, an audio device such as a speaker, any combination thereof, and any other device or devices suitable for providing user feedback.

In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the multi-modality applicator 104. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the multi-modality applicator 104 and/or the patient protection device described above. In yet other embodiments, the various components can be fixedly installed at a treatment site. Further details with respect to components and/or operation of multi-modality applicators 104, treatment units 106, and other components may be found in commonly-assigned U.S. Patent Publication No. 2008/0287839.

In operation, and upon receiving input to start a treatment protocol, the controller 114 can cause one or more power supplies 110, one or more treatment units 106, and one or more multi-modality applicators 104 to cycle through each segment of a prescribed treatment plan. In so doing, power supply 110 and treatment unit 106 provide coolant and power to one or more functional components of the applicator 104, such as thermoelectric coolers (e.g., TEC "zones"), to begin a cooling cycle and, for example, activate features or modes such as vibration, massage, vacuum, etc. Additionally, the energy generating unit 107 is used to generate and transfer electrical pulse or pulses to the electrodes in the one or more functional components of the applicator 104 to begin selectively electroporating cooled lipid-rich cells in the subcutaneous tissue in the target region of the subject 101.

Using temperature sensors (not shown) proximate to the one or more multi-modality applicators 104, the patient's skin, a patient protection device, or other locations or combinations thereof, the controller 114 can determine whether a temperature or heat flux is sufficiently close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the system may attempt to heat or cool the tissue to the target temperature or to provide a target heat flux, a sensor may measure a sufficiently close temperature or heat flux. If the target temperature has not been reached, power can be increased or decreased to change heat flux to maintain the target temperature or "set-point" selectively to affect lipid-rich subcutaneous adipose tissue.

When the prescribed segment duration expires, the controller 114 may apply the temperature and duration indicated in the next treatment profile segment. In some embodiments, temperature can be controlled using a variable other than or in addition to power.

In some embodiments, heat flux measurements can indicate other changes or anomalies that can occur during treatment administration. For example, an increase in temperature detected by a heat flux sensor can indicate a freezing event at the skin or underlying tissue (i.e., dermal tissue). An increase in temperature as detected by the heat flux sensors can also indicate movement associated with the applicator, causing the applicator to contact a warmer area of the skin, for example. Methods and systems for collection of feedback data and monitoring of temperature measurements are described in commonly assigned U.S. Pat. No. 8,285,390.

The multi-modality applicators 104 may also include additional sensors to detect process treatment feedback. For example, thermal sensors can be included on the multi-modality applicator 104 and/or the energy generating unit 107 to measure voltage and current that is delivered to the target region of the subject 101. Thermal sensor output can be used, by the controller 114 for example, to control the delivery of power to the electrodes, the temperature of the electrodes or the desired electrical field strength and location during a treatment session. Additional sensors may be included for measuring tissue impedance, treatment application force, tissue contact with the applicator and energy interaction with the skin of the subject 101 among other process parameters.

In one embodiment, feedback data associated with energy delivery and heat removal from lipid-rich cells in the subcutaneous layer can be collected in real-time. Real-time collection and processing of such feedback data can be used in concert with treatment administration to ensure that the process parameters used to alter or reduce subcutaneous adipose tissue are administered correctly and efficaciously.

According to examples of the system 100, the multi-modality applicator 104 enhances disruption of cooled adipose tissue through further cell interrogation, such as via electroporation. Further, the examples can provide reduced treatment time, reduced discomfort to the patient, and increased efficacy of treatment.

Examples of the system 100 may provide the multi-modality applicator 104 which damages, injures, disrupts or otherwise reduces subcutaneous lipid-rich cells generally without collateral damage to non-lipid-rich cells in the treatment region. In general, it is believed that lipid-rich cells selectively can be affected (e.g., damaged, injured, or disrupted) by exposing such cells to low temperatures that do not so affect non-lipid-rich cells. Moreover, as discussed above, electrical pulses can be administered simultaneously and/or in consecutive fashion to further selectively interrogate lipid-rich cells in the treatment region so as to beneficially and cosmetically alter subcutaneous adipose tissue. As a result, lipid-rich cells, such as subcutaneous adipose tissue, can be damaged while other cells in the same region are generally not damaged even though the non-lipid-rich cells at the surface may be subject to even lower temperatures. The mechanical energy provided by the applicator 104 may further enhance the effect on lipid-rich cells by mechanically disrupting the affected lipid-rich cells.

In some examples of the system 100, a cryoprotectant is used with the applicator 104 to, among other advantages, assist in preventing freezing of non lipid-rich tissue (e.g., dermal tissue) during treatment as is described in commonly-assigned U.S. Patent Publication No. 2007/0255362.

In one mode of operation, the applicator 104 may be configured to be a handheld device such as the device disclosed in commonly-assigned U.S. Pat. No. 7,854,754.

Applying the multi-modality applicator 104 with pressure or with a vacuum type force to the subject's skin or pressing against the skin can be advantageous to achieve efficient treatment. In general, the subject 101 has a body temperature of about 37° C., and the blood circulation is one mechanism for maintaining a constant body temperature. As a result, blood flow through the skin and subcutaneous layer of the region to be treated can be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the applicator with pressure, can improve the efficiency of tissue cooling and avoid excessive heat loss through the dermis and epidermis. Additionally, a vacuum can pull skin away from the body which can assist in cooling targeted underlying tissue.

By cooling the subcutaneous tissue to a temperature lower than 37° C., prior to or during electroporation of subcutaneous lipid-rich cells, these cells can selectively be damaged with clinically acceptable voltage pulses in voltage ranges lower than that required for electroporation without cooling. In general, the cells forming the epidermis and dermis of the subject 101 have lower amounts of lipids and are smaller in size compared to the underlying lipid-rich cells forming the subcutaneous tissues. Because non-lipid-rich cells usually can withstand colder temperatures better than lipid-rich cells and have higher transmembrane potentials, the subcutaneous lipid-rich cells can selectively be injured while maintaining the non-lipid-rich cells in the dermis and epidermis.

Figure 4:
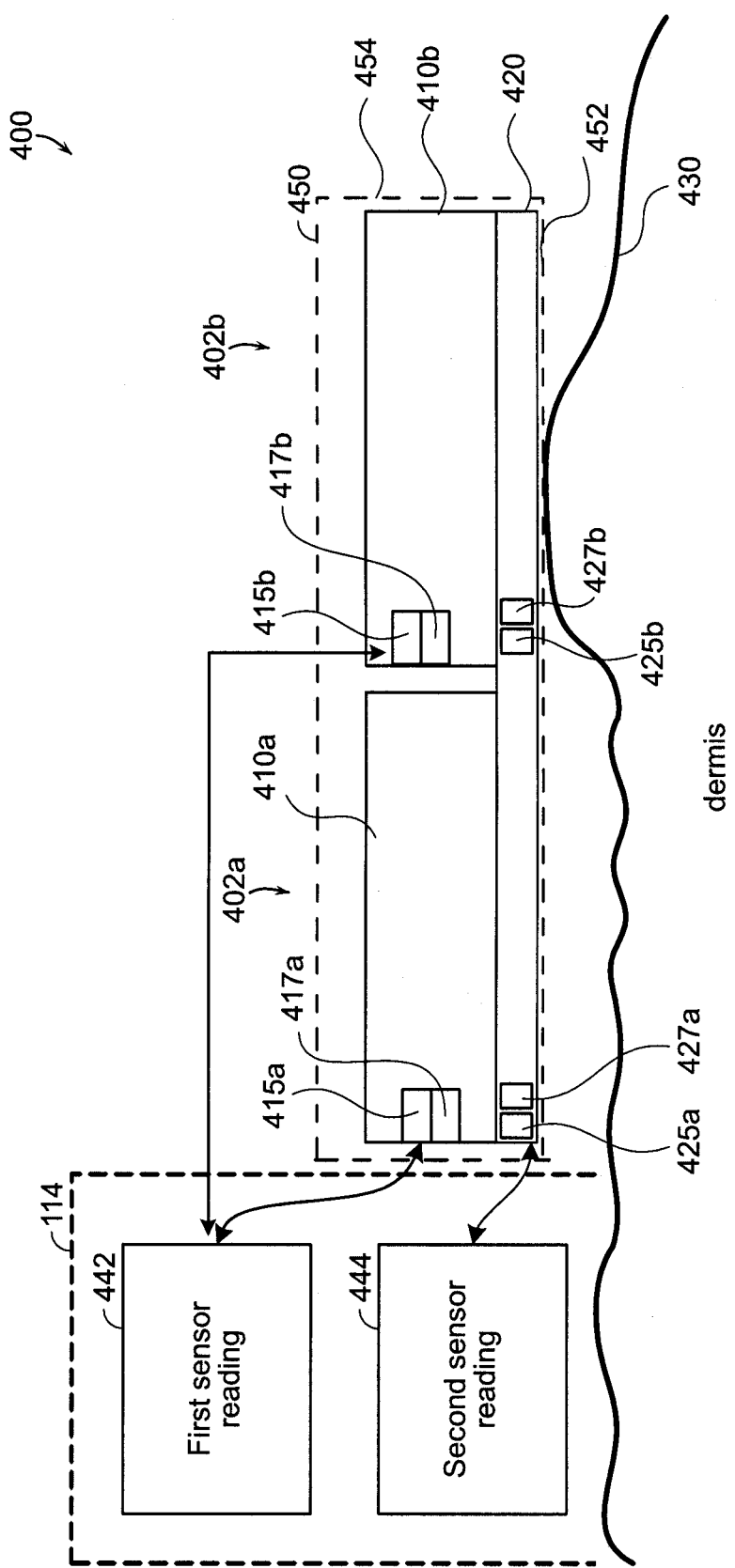
FIG. 4 is a partial cross-sectional view illustrating a multi-modality applicator suitable to be used in the system of FIG. 1 in accordance with embodiments of the technology.

FIG. 4 is a schematic, cross-sectional view illustrating a multi-modality applicator 400 for non-invasively removing heat from subcutaneous lipid-rich target areas of the subject 101 (FIG. 1) and for non-invasively applying energy to generate an electric field selectively to electroporate subcutaneous lipid-rich cells in the target area in accordance with an embodiment of the technology. The applicator 400 can include one or more applicator units 402 (shown individually as 402a and 402b) that can include one or more energy exchanging plates 410 (shown individually as 410a and 410b), and an interface layer 420. In one embodiment, the energy exchanging plates 410a, 410b are electrically conductive flat plate electrodes that can deliver bipolar electrical pulses generated by the energy generating unit 107 (FIG. 1).

Bipolar electrical pulses, such as high voltage or low voltage electrical pulses, generated by the energy generating unit 107 (FIG. 1) can be delivered to the energy exchanging plates 410a, 410b (e.g., spatially separated flat plate electrodes) via power line or other conductor cable. The energy exchanging plates 410a, 410b can be spatially separated within the multi-modality applicator 400 by a predetermined distance such that an electric field generated by delivery of the bipolar electrical pulses can penetrate the target region to a desirable depth within the tissue. For example, a positive electric field may be generated by delivering bipolar pulses to the cathode (e.g., plate 410a) and allowing return of the signal through the nearby anode (e.g., plate 410b). In other embodiments, a negative electric field can be generated by reversing the signal.

The energy exchanging plates 410a, 410b can contain one or more communication components 415 (shown individually as 415a and 415b) that communicate with the controller 114 to provide a first sensor reading 442 as described herein, and one or more sensors 417 (shown individually as 417a and 417b) that measure, e.g., temperature of the energy exchanging plates 410a, 410b, heat flux across a surface of or plane within the energy exchanging plates 410a, 410b or voltage readings. The interface layer 420 can be a plate, a film, a covering, a sleeve or other suitable materials described herein and may serve as the patient protection device described herein. The interface layer 420 is located between the energy exchanging plates 410a, 410b and the skin 430 of a subject (not shown), such as the skin of a patient receiving treatment via the multi-modality applicator 400. Other interface layers may be present.

The interface layer 420 can also contain one or more similar communication components 425 (shown individually as 425a and 425b) that communicate with the controller 114 to provide a second sensor reading 444 and one or more sensors 427 (individually shown as 427a and 427b) that measure, e.g., the temperature of different portions of the interface layer 420, heat flux across a surface of or plane within the interface layer 420, voltage readings or contact pressure with the skin 430 of the patient. For example, one or both of the communication components 415, 425 can receive and transmit information from the controller 114, such as temperature and/or heat flux information as determined by one or both of the sensors 417, 427. The sensors 417, 427 can be configured to measure a parameter of the interface without substantially impeding heat transfer between the energy exchanging plates 410a, 410b and the subject's skin 430. The applicator 400 can also contain power components and other components described with respect to FIG. 1 and related applications.

In certain embodiments, the multi-modality applicator 400 can include a dielectric sleeve 450 for contacting the patient's skin 430 and for achieving a more uniform distribution of electrical pulses, such as bipolar rectangular pulses, into the patient's underlying subcutaneous tissue. The sleeve 450 can include a first sleeve portion 452 and a second sleeve portion 454 extending from the first sleeve portion. The first sleeve portion 452 can contact and/or facilitate the contact of the multi-modality applicator 400 with the patient's skin 430, while the second sleeve portion 454 can be an isolation layer extending from the first sleeve portion 452. The second sleeve portion 454 can be constructed from latex, rubber, nylon, Kevlar®, or other substantially impermeable or semi-permeable material. The second sleeve portion 454 can prevent contact between the patient's skin 430 and the energy exchanging plates 410a, 410b, among other things.

The surface of the first sleeve portion 452 can include a dielectric or variable resistance material providing an insulator between the electrically conductive energy exchanging plates 410a, 410b and the interface layer 420 and the patient's skin 430. For example, the material can include material coated or comprised of Teflon®, silicon nitride, polysilanes, polysilazanes, polyimides (such as, e.g., Kapton® film) and other polymers or dielectric materials well known in the art. The capacitive effect of the dielectric layer (e.g., the first sleeve portion 452) can be controlled, for example, through sleeve thickness, surface area, the dielectric constant of the material and the electrical pulses generated. In some embodiments, the first sleeve portion 452 extends beyond the edges of the electrically conductive energy exchanging plates 410a, 410b and/or other electrodes such that the electrical pulses are required to flow through the dielectric material of the first sleeve portion 452. Further details regarding a suitable sleeve may be found in U.S. Patent Publication No. 2008/0077201.

In other embodiments, the multi-modality applicator 400 can include a belt that assists in forming a contact between the applicator 400 (such as via an interface layer 420) and the patient's skin 430. For example, the applicator 400 can include retention devices (not shown) coupled to a frame. The retention devices may be rotatably connected to the frame by a plurality of coupling elements that can be, for example, pins, ball joints, bearings, or other type of rotatable joints. Alternatively, the retention devices can be rigidly affixed to the end portions of heat exchanging element housings. Further details regarding a suitable belt device may be found in U.S. Patent Publication No. 2008/0077211.

In further embodiments, the multi-modality applicator 400 can include a vacuum (not shown) that assists in forming a contact between the applicator 400 (such as via the interface layer 420 or dielectric sleeve 450) and the patient's skin 430. For example, the applicator 400 can provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. Patent Application Publication No. 2008/0287839.

FIG. 5 is a schematic cross-sectional view of a multi-modality applicator 500 for non-invasively removing heat from subcutaneous lipid-rich target areas of the subject 101 (FIG. 1) and for non-invasively applying energy to generate an electric field selectively to electroporate subcutaneous lipid-rich cells in the target area in accordance with another embodiment of the technology. The applicator 500 includes a housing 501 having a vacuum cup 502 with a vacuum port 504 disposed in the vacuum cup 502. The housing 501 is coupled to or otherwise supports a first applicator unit 510a on one side of the cup 502, and a second applicator unit 510b on an opposing side of the cup 502. Each of the first and second applicator units 510a and 510b can include an electrically conductive flat plate electrode 512 (shown individually as 512a and 512b) and include an interface layer 514 (shown individually as 514a and 514b). The electrodes 512a, 512b can be configured to provide both cooling to the target region as well as to deliver energy from the energy generating unit 107 (FIG. 1) via power lines 109a, 109b (FIG. 1). As such, the flat plate electrodes 512a, 512b can be similar to the energy exchanging plates 410a, 410b described above with reference to FIG. 4.

The interface layers 514a and 514b are adjacent to the flat plate electrodes 512a and 512b, respectively. Similar to the interface layer 420 illustrated in FIG. 4, the interface layers 514a and 514b can be plates, films, a covering, a sleeve or other suitable materials located between the flat plate electrodes 512a and 512b and the skin (not shown) of a subject. In one embodiment, the interface layers 514a and 514b can serve as patient protection devices as described herein. The interface layers 514a and 514b can include communication components (not shown) and sensors (not shown) similar to those described with respect to the interface layer 412 of FIG. 4 for communicating with the controller 114 (FIG. 1).

In operation, the rim 516 of the vacuum cup 502 is placed against the skin of a subject (not shown) and a vacuum is drawn within the cup 502. The vacuum pulls the tissue of the subject into the cup 502 and coapts the target area with the interface layers 514a and 514b of the corresponding first and second applicator units 510a, 510b. One suitable vacuum cup 502 with cooling units is described in U.S. Pat. No. 7,367,341.

The applicator units 510a and 510b can be in communication with the controller 114, treatment unit 106, energy generating unit 107 and power supply 110 (FIG. 1) such that the flat plate electrodes 512a, 512b can provide cooling and electrical pulses or other energy to the target region based on a predetermined or real-time determined treatment protocol. For example, the electrodes 512a, 512b can first be cooled to cool the adjacent tissue of the target region to a temperature below 37° C. (e.g., to a temperature in the range of between about −20° C. to about 20° C.). The flat plate electrodes 512a, 512b can be cooled using Peltier devices, cooling channels (e.g., channels through which a chilled fluid flows), cryogenic fluids, or other similar cooling techniques. In one embodiment, the flat plate electrodes 512a, 512b are cooled to a desired treatment temperature (−15° C., −10° C., 0° C.) to cool subcutaneous lipid-rich cells. The lipid-rich cells can be maintained at a sufficiently low temperature to damage or destroy the lipid rich cells.

The electrodes 512a, 512b can also, either concurrently to cooling or sequential to the cooling step, deliver electrical pulses, such as bipolar pulses in the range of about 50 V to about 900 V with a duration of about 10 microseconds to about 1 milliseconds. In some embodiments, cooling can be continued or re-administered to the target region following the energy application to further interrogate the lipid-rich cells, such as to prevent pores in the cell membrane (e.g., caused by electroporation) from closing. The energy generating unit 107 and/or power supply 110 (FIG. 1) can be used to apply voltage across the target region enclosed within the cup 502 by the vacuum 504. The bipolar pulses can generate an electric field that travels substantially uniformly between the electrodes 512a and 512b. In various embodiments, the electric field can have either a positive (+) or negative (−) polarity. For example, the flat plate electrode 512a can be charged positively and the electrode 512b can be charged negatively to perform electroporation. The applied voltage can cause pore formation in cell membranes, and particularly in lipid-rich cells.

Although a noninvasive applicator unit is illustrated and discussed with respect to FIGS. 4 and 5, minimally invasive applicators may also be employed. In such a case, the applicator and patient protection device may be integrated. As an example, a cryoprobe and/or electrode that may be inserted directly into the subcutaneous adipose tissue to cool or freeze the tissue and/or deliver energy is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007/0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004/0215294, entitled "CRYOTHERAPY PROBE"; U.S. Pat. No. 7,083,612, entitled "CRYOTHERAPY SYSTEM"; and U.S. Publication No. 2005/0261753, entitled "METHODS AND SYSTEMS FOR CRYOGENIC COOLING".

FIG. 6 is a schematic cross-sectional view of a multi-modality applicator 600 for non-invasively removing heat from subcutaneous lipid-rich target areas of the subject 101 (FIG. 1) and for minimally-invasively or invasively applying energy to generate an electric field selectively to electroporate subcutaneous lipid-rich cells in the target region in accordance with a further embodiment of the technology. The applicator 600 of FIG. 6 includes features generally similar to the features of the multi-modality applicator 500 described above with reference to FIG. 5. For example, the applicator 600 includes a housing 601 having a vacuum cup 602 with a vacuum port 604 disposed in the vacuum cup 602, wherein the housing 601 is coupled to or otherwise supports a first applicator unit 610a on one side of the cup 602, and a second applicator unit 610b on an opposing side of the cup 602. However, in the embodiment shown in FIG. 6, the applicator units 610a, 610b include cooling plates 612 (shown individually as 612a and 612b) and electrode arrays 614 (shown individually as 614a and 614b) for minimally invasively or invasively delivering electrical pulses to the target region.

The electrode arrays 614a, 614b can include one or more retractable tissue piercing electrodes 616. The retractable tissue piercing electrodes 616 can, in one embodiment, be electrode needles that move inwardly (indicated by arrows 618 and 620) after the tissue is pre-cooled and numb by the cooling and/or by other means (topical agents such as lidocane, injectable agents, etc.). Once inserted into the tissue of the target region at a desirable depth, the tissue piercing electrodes 616 can deliver a desired voltage pulse (s) across the tissue to achieve selective electroporation of subcutaneous lipid-rich cells. Once electroporation has occurred, the tissue piercing electrodes 616 can be withdrawn and retracted into the applicator units 610a, 610b while the cooling plates 612 can continue to maintain the target region tissue at a cold temperature (e.g., below 37° C.). The applicator 600 can include one or more actuators, drive devices, or other components that move the retractable tissue piercing electrodes 616. The first and second applicator units 610a, 610b may also, optionally, include an interface layer (not shown), a dielectric layer (not shown) or both.

C. Additional Embodiments

In further embodiments, the system 100 and any one of the multi-modality applicators 104, 400, 500 and 600 can be configured to cool tissue to enhance lysis of lipid-rich cells caused by RF pulses, micropulses, ultrasound pulses, or other types of delivered energy. For example, as has been disclosed herein with respect to the present technology, pore formation, pore growth, and cell membrane permeability, such as that for large lipid-rich cells in subcutaneous adipose tissue, are dependent and/or correlate with the temperature of the target cells prior to, during, and after the electrical pulse interrogation of the cells. In one embodiment, the objective of subcutaneous adipose tissue alteration and reduction therapy can be achieved by keeping cell pores open for periods of time (e.g., minutes) longer than electrical energy administration to allow for greater cell lysis and cell death. Accordingly, embodiments described herein can achieve this objective by in vivo cooling of the subcutaneous lipid-rich cells pre-, during and post-electrical energy application. In various arrangements, subcutaneous adipose tissue reduction can be enhanced with electroporation when compared to cooling alone. Likewise, voltage applied across a target tissue region to achieve electroporation of subcutaneous lipid-rich cells can be at a lower voltage gradient when applied to cooled cells than when compared to non-cooled cells.

Features of the multi-modality system and device components described above and illustrated in FIGS. 1-6 can be modified to form additional embodiments configured in accordance with the present technology. For example, the multi-modality applicator 400 illustrated in FIG. 4 and other cryotherapeutic devices described above and illustrated in FIGS. 5 and 6 can be configured with a single unipolar electrode for administering monopolar electrical pulses through target tissue. Similarly, the multi-modality applicators described above and illustrated in FIGS. 5 and 6 can be configured to change or otherwise alter a distance between the flat plate electrodes, for example, as necessary to control a specific applied voltage across target tissue to be treated. For example, the distance between the electrodes can be reduced in some instances to reduce an applied voltage effective for electroporation.

In other examples, the multi-modality system and devices described herein can be combined with additional modalities to enhance the therapeutic and cosmetic effects on and alterations (e.g., reduction) of subcutaneous adipose tissue and/or enhance preservation or viability of non-lipid-rich cells in the target region. These can include, for example, delivery of drugs, vaccines and gene therapy that can, for example, be introduced into the electroporated cells via the open pores.

Features of the multi-modality system and device components described above also can be interchanged to form additional embodiments of the present technology. For example, the retractable and/or minimally invasive electrodes 616 of the applicator units 610a, 610b illustrated in FIG. 6 can be incorporated into the energy exchanging plates 410a, 410b shown in FIG. 4. In certain embodiments, the multi-modality applicators (e.g., applicator 400, 500 and 600) can be configured without interface layers or dielectric layers between the energy exchange plates, flat plate electrodes, or cold plates and the skin of the patient.

D. Multi-Modality Treatment Methods

The system 100 (FIG. 1) can be used to perform several multi-modality treatment methods. Although specific examples of methods are described herein, one skilled in the art is capable of identifying other methods that the system could perform. Moreover, the methods described herein can be altered in various ways. As examples, the order of illustrated logic may be rearranged, sub-stages may be performed in parallel, illustrated logic may be omitted, other logic may be included, etc.

Figure 7:
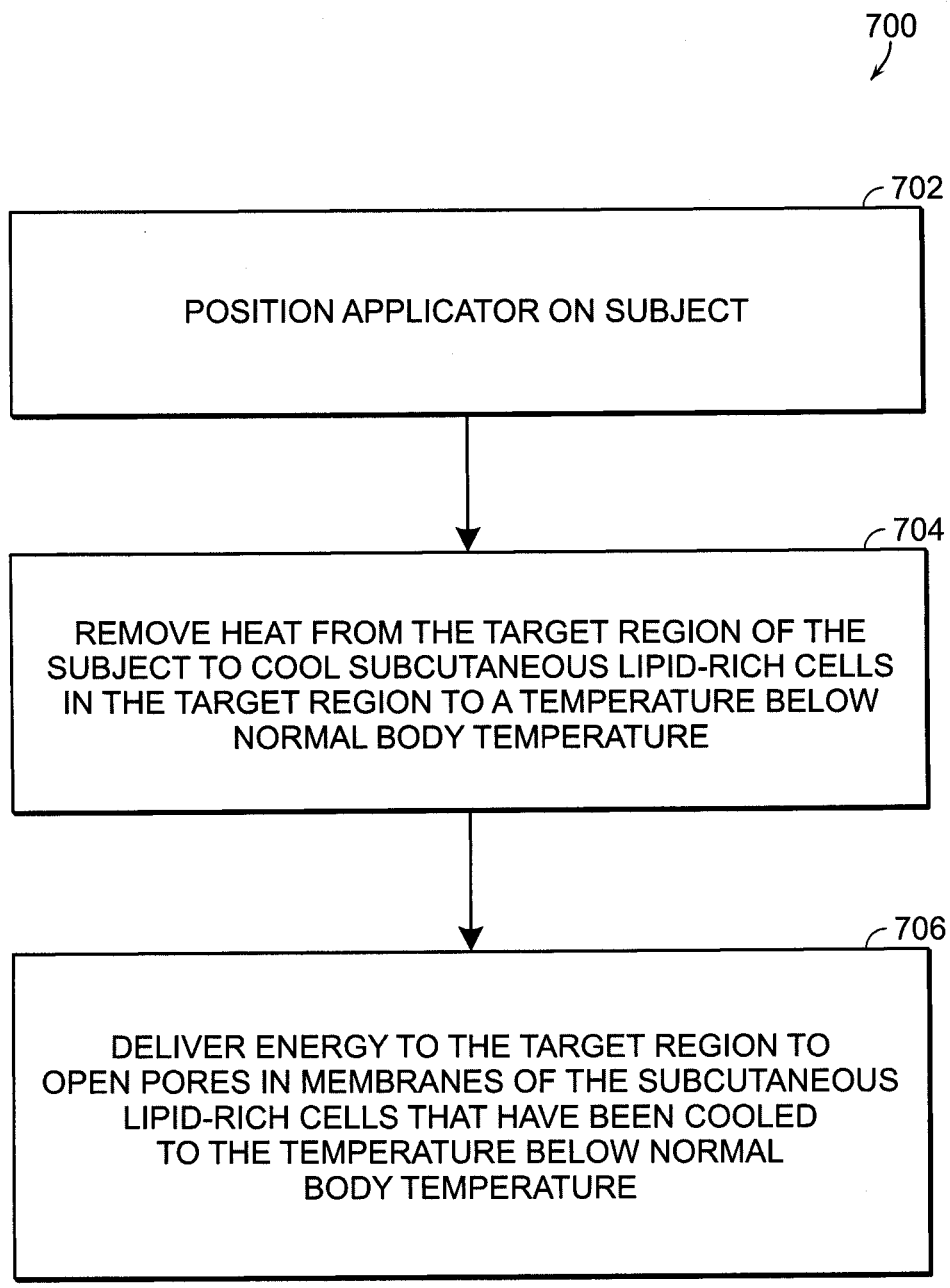
FIG. 7 is a flow diagram illustrating a method for non-invasively removing heat from a target region and applying energy to generate an electric field for selectively electroporating subcutaneous lipid-rich cells in the target region in accordance with a further embodiment of the technology.

FIG. 7 is a flow diagram illustrating a method 700 for non-invasively removing heat from subcutaneous lipid-rich target areas of a subject and for applying energy to generate an electric field for selectively electroporating subcutaneous lipid-rich cells in the target area in accordance with a further embodiment of the technology. Even though the method 700 is described below with reference to the multi-modality treatment system 100 of FIG. 1 and the multi-modality applicators 104, 500 and 600 of FIGS. 4, 5 and 6, respectively, the method 700 may also be applied in other treatment systems with additional or different hardware and/or software components.

As shown in FIG. 7, an early stage of the method 700 can include positioning one or more applicators on the subject (block 702). For example, surfaces of the applicator unit(s) can couple with the surface of the subject's skin at a target region. In one embodiment, the applicator unit can include an energy exchanging plate, a plate electrode or cooling plate. In another embodiment, the surface of the applicator unit can be the surface of an interface layer or a dielectric layer. Coupling of the surface(s) of the applicator unit(s) to the surface of the skin can be facilitated by using restraining means, such as a belt or strap. In other embodiments, a force (e.g., vacuum or suction force) can be used to positively couple the patient's skin at the target region to the surfaces. Additionally, coupling the applicator unit(s) to the subject's skin can also include providing a cryoprotectant to the patient's skin as is described in commonly assigned U.S. Patent Publication No. 2007/0255362.

The method 700 can also include removing heat from the target region of the subject (e.g., human or animal patient) during a treatment process selectively to cool subcutaneous lipid-rich cells in the target region to a temperature below normal body temperature (block 704). For example, the lipid-rich tissue can be cooled to a temperature below about 37° C., below about 20° C., below about 10° C. or below about 0° C. such that lipid-rich cells are affected without substantially affecting non-lipid-rich cells.

In block 706, the method 700 also includes delivering electrical energy to the target region to produce a pulsed electric field in an amount sufficient to create and/or open pores in membranes of the subcutaneous lipid-rich cells that have been cooled to the temperature below normal body temperature, wherein the pores compromise either cell volume or cell viability. In some embodiments, the electrical energy may be monopolar while in other embodiments it may be bipolar. In some embodiments, the electrical energy includes an applied voltage between two or more electrodes. In one embodiment, the applied voltage can be delivered at a voltage range from about 50 V to about 900 V with a pulse duration of about 10 microseconds to about 1.0 milliseconds. In some embodiments, delivering electrical energy to the target region affects subcutaneous lipid-rich cells without substantially affecting non-lipid-rich cells. In various embodiments, energy application parameters can be predetermined such that the electrical energy delivered to the target region irreversibly creates and/or opens pores in the membranes of the subcutaneous lipid-rich cells, thereby allowing the subcutaneous lipid-rich cells to lyse. In another example, energy application parameters can be predetermined such that the electrical energy delivered to the target region reversibly creates and opens pores in the membranes of the subcutaneous lipid-rich cells, thereby allowing a lipid volume of the subcutaneous lipid-rich cells to be reduced. One of ordinary skill in the art will recognize that the voltage applied across the tissue of the target region can be calculated according to the tissue characteristics and thickness, desired depth of the electric field, the distance between positive (+) and negative (−) electrodes, and/or the pulse duration and frequency among other factors. In some aspects, delivering energy to the target region to produce a pulsed electric field includes selectively electroporating lipid-rich cells that have been cooled to a temperature below approximately 10° C. to about 15° C.

Removing heat from the target region may occur before delivery of the energy to the target region; however in other embodiments, removing heat from the subcutaneous layer in the target region may occur simultaneously to energy delivery. For example, the treatment method 700 may include a single stage or multiple stages of delivering energy with each such stage occurring simultaneously with a single stage or multiple stages of removing heat from the lipid-rich cells in the target region. In some treatment regimes, removing heat from the target region can precede and occur simultaneously to energy delivery to the same region, and optionally, heat removal can continue post-energy delivery.

Alternatively, removing heat from the subcutaneous layer and delivering the energy to the target region may occur sequentially. For example, the method 700 may consist of a single stage of removing heat from the lipid-rich cells in the target region that ceases prior to a single stage of delivering energy to the lipid-rich cells in the target region. Additionally, such sequential application of the aforementioned stages may occur multiple times so that multiple non-overlapping stages of energy delivery and heat removal occur.

Another way that method 700 may be accomplished is by periodically or intermittently delivering energy to the target region of the subject simultaneously with removing heat. For example, method 700 may comprise a single stage of removing heat from the lipid-rich cells in the target region during which stage energy is delivered in multiple stages in a regular, periodic fashion or in a less regular, intermittent fashion.

Alternatively, method 700 may include a single stage of delivering energy to the target region during which stage removing heat from the target region is accomplished in multiple stages in a regular, periodic fashion or in a less regular, intermittent fashion.

The duration of delivering the energy and/or amount of voltage applied to the target region according to the embodiments described herein may vary depending on the location of the target region, the degree of warming required, the power setting, whether the energy is delivered as bipolar or monopolar pulses, the parameters of the stage of removing heat to reduce to selectively affect or compromise lipid-rich cells in the subcutaneous layer, and other parameters.

Such a duration may be calculated and described in terms of a single application of energy or cumulatively as summed over the course of more than one application of energy. For example, a single application of energy as described herein may range in duration from 10 microseconds to one or more milliseconds or more. In contrast, the duration of removing heat from the lipid-rich cells in the target region, such as described for example in U.S. Pat. No. 7,367,341, can have a duration of a period of application between about 1 minute and about 2 hours, between about 1 minute and about 1 hour, between about 1 minute and about 50 minutes, or between about 1 minute and about 40 minutes, or between about 1 minute and about 30 minutes, or between about 1 minute and about 20 minutes. Still another embodiment results in a single application of cooling of between about 5 minutes and about 15 minutes. Applying energy in multiple stages as described herein, whether in periodic or intermittent fashion, for example, may also range cumulatively over those multiple stages in duration from a microsecond, a millisecond or less to several seconds or more.

Various aspects of the method 700 can include a cosmetic treatment method for treating the target region of a human subject's body to achieve a cosmetically beneficial alteration of subcutaneous adipose tissue. Such a method could be administered by a non-medically trained person.

E. Suitable Computing Environments

Figure 8:
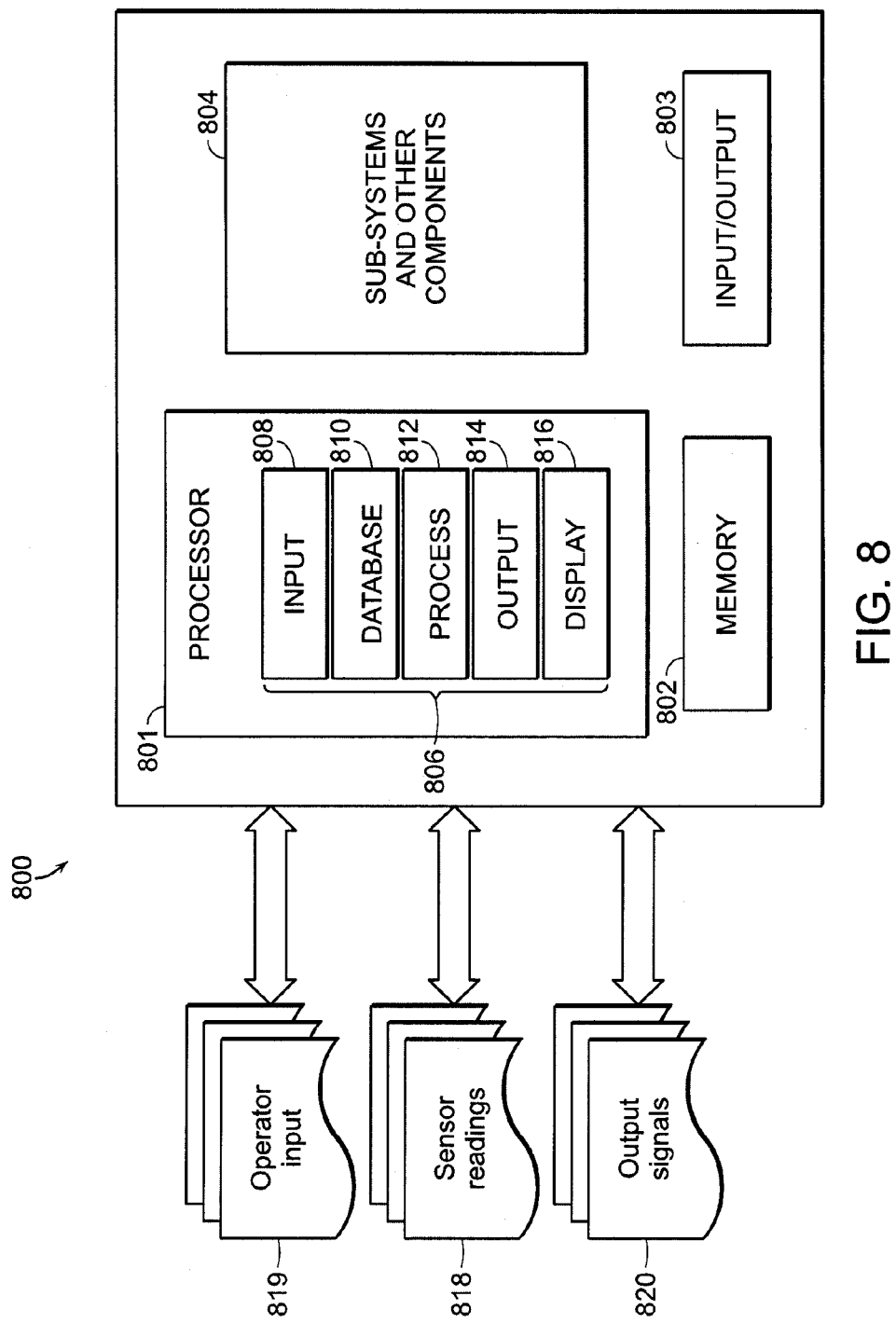
FIG. 8 is a schematic block diagram illustrating computing system software modules and subcomponents of a computing device suitable to be used in the system of FIG. 1 in accordance with an embodiment of the technology.

FIG. 8 is a schematic block diagram illustrating subcomponents of a computing device 800 in accordance with an embodiment of the disclosure. The computing device 800 can include a processor 801, a memory 802 (e.g., SRAM, DRAM, flash, or other memory devices), input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 8, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices described above with respect to FIG. 1, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors (e.g., the temperature measurement components 417 and 427 of FIG. 4) and/or other data sources, and the output module 814 can communicate operator input to external computing devices and control variables to the controller 114 (FIG. 1). The display module 816 can be configured to convert and transmit processing parameters, sensor readings 818, output signals 820, input data, treatment profiles and prescribed operational parameters through one or more connected display devices, such as a display screen, printer, speaker system, etc. A suitable display module 816 may include a video driver that enables the controller 114 to display the sensor readings 818 or other status of treatment progression on the output device 120 (FIG. 1).

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

F. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Some of the functional units described herein have been labeled as modules, in order to more particularly emphasize their implementation independence. For example, modules (e.g., modules discussed in connection with FIG. 8) may be implemented in software for execution by various types of processors. An identified module of executable code may, for instance, comprise one or more physical or logical blocks of computer instructions which may, for instance, be organized as an object, procedure, or function. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

I claim:

1. A system for affecting lipid-rich cells in a region of a human subject's body, comprising:
    a treatment unit configured to house a coolant;
    an energy generating unit;
    an applicator in fluid communication with the treatment unit and in electrical communication with the energy generating unit; and
    a controller in communication with the treatment unit and the energy generating unit, wherein the controller has memory containing instructions that, when executed by the controller, cause the applicator to:

reduce a temperature of a target region beneath the epidermis of the subject to reduce a temperature of subcutaneous lipid-rich cells in the target region to a second temperature less than 37° C.; and after reducing the temperature of the target region, start applying energy across the target region such that the applied energy causes pores to form in membranes of the subcutaneous lipid-rich cells, which are at a temperature lower than 37° C.

2. The system of claim 1 wherein the instructions cause the applicator to apply voltage across the target region to produce a pulsed electric field in an amount sufficient to form the pores in the membranes of the subcutaneous lipid-rich cells.

3. The system of claim 2 wherein the amount of voltage sufficient to form the pores is approximately 10% to about 30% less than the amount of voltage sufficient to form pores in membranes of the subcutaneous lipid-rich cells prior to reducing the temperature to the second temperature.

4. The system of claim 2 wherein the pulsed electric field is produced in an amount insufficient to form pores in membranes of non-lipid-rich cells in the target region.

5. The system of claim 1 wherein the applicator is configured to apply voltage across the target region to produce a pulsed electric field in an amount sufficient to irreversibly open pores in the membranes of the subcutaneous lipid-rich cells, thereby causing the subcutaneous lipid-rich cells to die.

6. The system of claim 1 wherein reducing a temperature of the target region includes cooling the subcutaneous lipid-rich cells in the target region to a temperature below 10° C.

7. The system of claim 1 wherein the energy generating unit is a radiofrequency (RF) energy generating unit, wherein the controller is in communication with the RF energy generating unit, and wherein the controller has instructions for causing the applicator to deliver RF energy from the RF energy generating unit to the target region selectively to affect lipid-rich cells in the target region.

8. The system of claim 1 wherein the applicator is configured to apply voltage across the target region at a voltage range from about 50 V to about 900 V.

9. The system of claim 8 wherein the applicator is configured to apply voltage across the target region in pulses of duration ranging from about 1 microsecond to about 1 millisecond.

10. The system of claim 1 wherein the applicator is configured to apply bipolar electrical pulses across the target region.

11. The system of claim 1 wherein the applicator includes a plate electrode in thermal communication with the treatment unit and in electrical communication with the energy generating unit.

12. The system of claim 11 wherein the plate electrode is a first flat plate electrode facing a first direction, wherein the applicator includes a second plate electrode facing a second direction, and wherein the second direction is substantially opposite the first direction.

13. The system of claim 1 wherein the applicator includes a cooling plate in thermal communication with the treatment unit and an electrode array in electrical communication with the energy generating unit, and wherein the electrode array includes a plurality of retractable tissue piercing electrodes.

14. The system of claim 1 wherein the controller has instructions for causing the applicator to maintain the second temperature while applying energy across the target region.

15. The system of claim 1 wherein the controller has instructions for causing the applicator to maintain the second temperature for a period after applying energy across the target region.

16. The system of claim 15 wherein the period is between about 1 minute and about 1 hour.

17. The system of claim 1 wherein the applicator includes one or more thermoelectric elements positioned to provide individually controlled heat exchanging zones while coolant from the treatment unit flows through the applicator.

18. The system of claim 1 wherein the applicator includes one or more thermoelectric elements controlled by the controller and positioned to cool the target region.

19. The system of claim 1 wherein the instructions cause the applicator to cool the subcutaneous lipid-rich cells from a normal temperature to less than about 10° C. before forming the pores, and maintain the temperature of the subcutaneous lipid-rich cells below 10° C. after forming the pores.

20. A system for affecting subcutaneous tissue in a target region of a human subject's body, comprising:

an energy generating unit;

an applicator in electrical communication with the energy generating unit and configured to non-invasively remove heat from the subcutaneous tissue and deliver energy to the target region; and a controller in communication with the energy generating unit and including memory, the memory containing instructions for causing the system to:

deliver the energy from the applicator to the target region to form pores in membranes of subcutaneous cells of the subcutaneous tissue while the subcutaneous cells are below 37° C., and use the applicator to— reduce a temperature of the subcutaneous tissue from a normal temperature to less than about 37° C. before forming the pores, and/or maintain the temperature of the subcutaneous tissue at less than about 37° C. after forming the pores.

21. The system of claim 20 wherein the applicator is configured to maintain the temperature of the subcutaneous tissue at a temperature below 0° C. while delivering the energy.

22. The system of claim 20 wherein the applicator is configured to apply one or more of radiofrequency (RF) pulses, ultrasound pulses, high frequency ultrasound (HIFU) phased signals, and microwave pulses.

23. The system of claim 20 wherein the applicator has cooling electrodes which transfer heat away from the target region to reduce the temperature of the target region and which are operable to apply voltage across the target region to produce a pulsed electric field that causes the formation of the pores.

24. A system for affecting subcutaneous tissue in a target region of a human subject's body, comprising:

a tissue-cooling applicator configured to monitor the target region and to deliver energy to the target region; and a controller including memory storing instructions that, when executed by the controller, cause the tissue-cooling applicator to monitor the temperature of the target region, non-invasively cool the target region to a temperature lower than 20° C., and deliver energy from the tissue-cooling applicator to the target region such that the energy causes pores to form in membranes of subcutaneous cells at the target region while the subcutaneous cells are cooler than 37° C.

25. The system of claim 24 wherein the instructions, when executed by the controller, cause the tissue-cooling applicator to cool and deliver energy to the target region such that subcutaneous lipid-rich cells at the target region are substantially affected while non-lipid-rich cells at the target region are not substantially affected.

26. The system of claim 24 wherein the instructions, when executed by the controller, cause the tissue-cooling applicator to cool the target region for a cooling period between 1 minute and 2 hours and to deliver the energy during the cooling period.

27. The system of claim 24 wherein the instructions, when executed by the controller, cause the tissue-cooling applicator to deliver a sufficient amount of the energy to the target region to cause formation of the pores, which cause the lipid-rich cells to die.

28. The system of claim 24 wherein the controller includes a processor for executing the instructions.

* * * * *